United States Patent [19]

Keunecke et al.

[11] 4,263,211
[45] Apr. 21, 1981

[54] PROCESS FOR THE RECOVERY OF MALEIC ANHYDRIDE FROM GASES CONTAINING MALEIC ANHYDRIDE

[75] Inventors: Gerhard Keunecke, Geyen; Anton Klopfer, Cologne; Herbert Krimphove, Pulheim; Lothar Sterck, Hürth, all of Fed. Rep. of Germany

[73] Assignee: Davy International Aktiengesellschaft, Frankfurt, Fed. Rep. of Germany

[21] Appl. No.: 130,367

[22] Filed: Mar. 14, 1980

[30] Foreign Application Priority Data

Mar. 16, 1979 [DE] Fed. Rep. of Germany ....... 2910385

[51] Int. Cl.$^3$ .......................................... C07D 307/60
[52] U.S. Cl. ................................................. 260/346.76
[58] Field of Search ................................... 260/346.76

[56] References Cited

U.S. PATENT DOCUMENTS 3,865,849   2/1973   Garkisch et al. ............... 260/346.76

Primary Examiner—Henry R. Jiles
Assistant Examiner—Bernard Dentz

[57] ABSTRACT

An improved process is provided for the recovery and storage of maleic anhydride from maleic anhydride-containing gases. Such gases are scrubbed with a water or maleic acid scrubbing solution in a scrubbing zone to form a maleic acid-containing solution. This maleic acid-containing solution is then concentrated and dehydrated in an evaporation zone and a dehydration zone, respectively, to form maleic anhydride. The maleic anhydride so formed is then purified by distillation in a distillation zone. The evaporation, dehydration, and distillation steps are all carried out under a vacuum maintained by withdrawing gases containing organic and water vapor from said evaporation, dehydration and distillation zones using jet pumps propelled by pressurized air. The vapor-containing gases so removed are admixed with the pressurized air pump propellant streams, and this mixture is then introduced into the scrubbing zone for the maleic anhydride-containing gases. Vapor-containing gases may also be sucked by the jet pumps from maleic anhydride storage vessels, and such vapor-containing gases may also then be introduced into the scrubbing zone.

7 Claims, 1 Drawing Figure

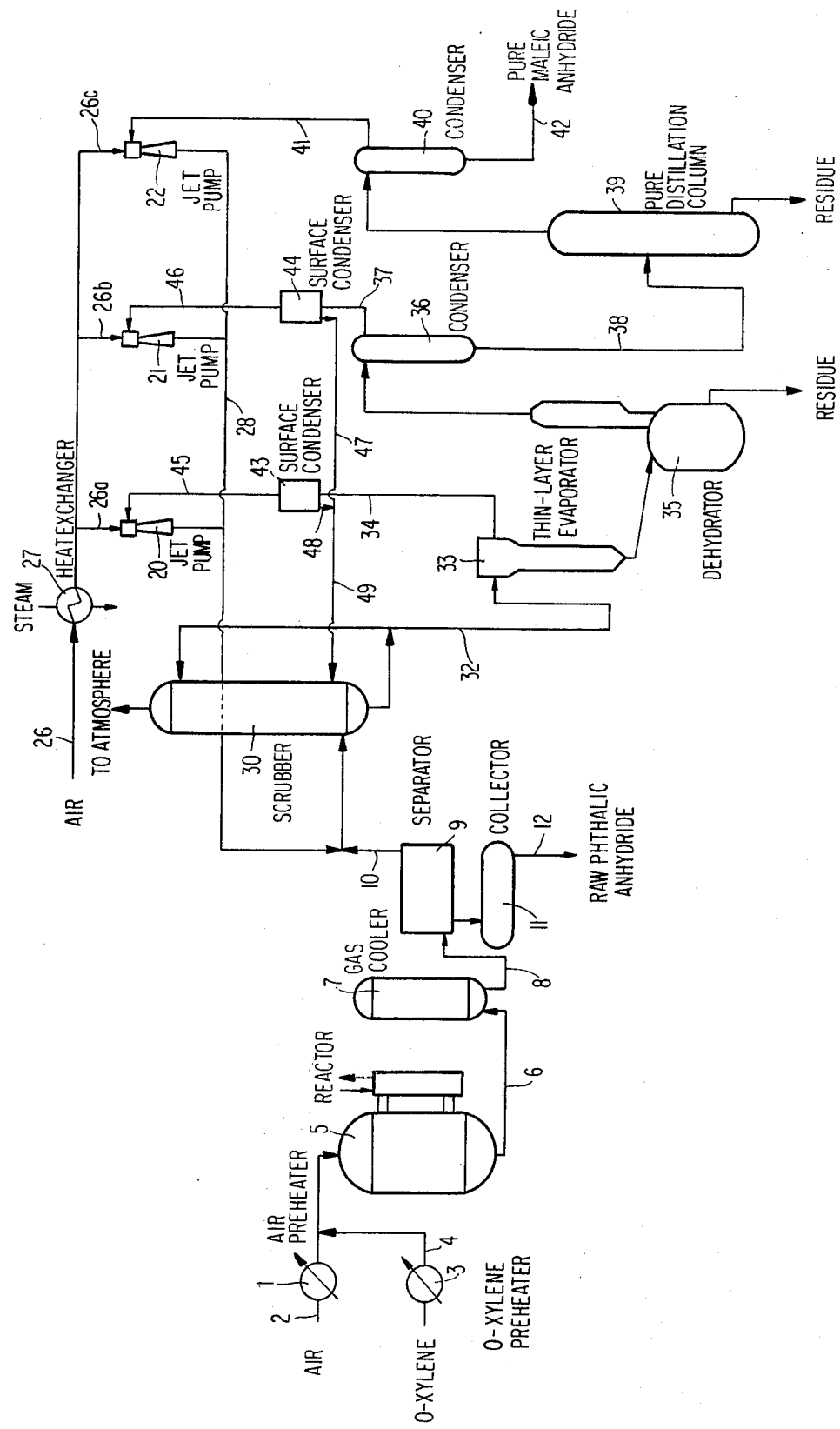

PROCESS FOR THE RECOVERY OF MALEIC ANHYDRIDE FROM GASES CONTAINING MALEIC ANHYDRIDE

The present invention relates to a process for the recovery of maleic anhydride from gases which contain maleic anhydride. Such gases include the reaction gases remaining from the catalytic oxidation of benzene, C-4 hydrocarbons, or o-xylene, after the condensation or, as the case may be, desublimation of raw maleic anhydride or phthalic anhydride from such gases. Removal of the residual maleic anhydride from such gases is brought about by scrubbing the reaction gases in a scrubbing zone with water or an aqueous maleic acid solution, by concentrating and dehydrating the scrubbing solution which contains maleic acid to form maleic anhydride and by thereafter purifying the maleic anhydride by distillation. Such concentration and/or dehydration and/or distillation is performed in evaporation, dehydration and distillation zones respectively, under a vacuum which is maintained by means of suction removal of gases containing organic and water vapor using jet pumps.

In the catalytic oxidation of o-xylene to form phthalic anhydride, maleic anhydride arises as a secondary product. The maleic anhydride formed is in part separated from the reaction gas with the phthalic anhydride and in part remains as residue in the waste gas from the phthalic anhydride separator. To recover this residual maleic anhydride from the separator waste gas and to avoid the discharge of impurities into the air, most modern plants remove the maleic anhydride from the separator waste gas by scrubbing such gas with aqueous solutions, thereby providing a diluted, e.g. 25% maleic acid solution. To recover pure maleic anhydride, this scrubbing solution is first concentrated by evaporation in an evaporation zone; the 100% maleic acid thus obtained is then dehydrated in a dehydration zone and the resulting still impure maleic anhydride is purified by distillation in a distillation zone. Concentration, dehydration, and distillation are performed under a vacuum, for example, at pressures in the area of 50 to 500 mm Hg. Heretofore, the vacuum has generally been produced with one or two-stage jet pumps or liquid seal pumps. A scrubbing condenser is coupled to the jet pumps. In such a condenser, the driving steam for the pumps, along with the absorbed gases and vapors, are condensed by means of injection of cooled water. This provides an aqueous maleic acid of low concentration, which solution is pumped back in a cycle to the scrubbing condensers by way of the coolers. The excess weak acid is added to the waste gas scrubbing solution. This process is costly in terms of the apparatus it requires. The solution injected into the scrubbing condenser coupled with the jet pumps must be constantly circulated and simultaneously cooled. To some extent, a scrubbing condenser must be placed before the jet pumps in order to cool the vapors sucked into the vacuum pipe and to partially precipitate the organic components thereof in order to reduce the danger of precipitation in the steam jets. Similar difficulties arise when the vacuum is maintained with liquid seal pumps.

The objective of the present invention is to reduce the apparatus costs and operating expenses in the process by which maleic anhydride is recovered from maleic anhydride-containing gases by the procedure of scrubbing the gases with water or with a maleic acid solution and by thereafter further processing the scrubbing solution into maleic anhydride. In addition, operation of the process apparatus is to be simplified.

These objectives are realized in the present invention by employing compressed air as a propellant for the jet pumps maintaining the vacuum as hereinbefore described and by introducing this air, charged with sucked organic-containing vapors, into the gas scrubbing zone. The entire quantity of organic-containing vapors and gases withdrawn from the maleic anhydride processing stages is sucked into the vacuum lines by the jet pumps, after which a large portion of such vapors, primarily water vapor, is condensed in a surface condenser(s). The propellant air, which is admixed with the remaining sucked gases and vapors recovered from the maleic anhydride processing stages, is introduced into the gas scrubbing solution, along with those reaction gases which are being treated and which contain residual maleic anhydride. Such reaction gases can be formed, for example, in the production of maleic anhydride from benzene or C-4 hydrocarbons, preferably after partial condensation of the maleic anhydride from the gas. Such reaction gases can also be formed in the production of phthalic anhydride from o-xylene after separation of the phthalic anhydride therefrom.

The charged propellant air returned to the reaction gas scrubbing zone can be combined with this maleic anhydride-containing reaction gases, or the reaction gases can be separately introduced into the scrubbing zone. By returning the vapors removed by suction along with the propellant air, the weak-acid cycle, which is necessary when steam jet suction units or liquid seal pumps are employed, can be omitted. In the process of the present invention, the water produced in the surface condensers is introduced directly to the gas scrubbing tower.

Ideally the pressurized air used as propellant for the vacuum-creating pumps is heated to temperatures between 30° and 200° C., preferably between 100° and 200° C. before introduction into the pumps. Such heating prevents condensation in the jet pumps, and in the lines thereafter, of the vapors sucked into the jet pumps. Disturbances in pump operation are thereby minimized. Operation of the system is generally performed with a propellant air pressure in the range of from about 1 to 20 atmospheres, more preferably from about 4 to 10 atmospheres.

In a preferred embodiment of the invention herein, the vapors are sucked into the pumps from the vacuum-operated stages of the scrubbing solution processing system, after considerable condensation of the water and/or, as the case may be, maleic anhydride, evaporated in such stages. Thus costs for the weak-acid cycle are eliminated.

In another particularly advantageous arrangement, the gases and vapors are sucked by jet pump suction units from all of those plant vessels which contain maleic anhydride and such gases and vapors are then returned to the gas scrubbing zone. In this fashion, the release of maleic anhydride from its storage vessels into the atmosphere is avoided. This procedure thus eliminates environmental pollution and product loss as well. Respiration of these maleic anhydride-containing vessels is most effectively performed with a heated gas, e.g. nitrogen, so as to prevent condensation of the maleic anhydride in the suction lines.

In the drawing, the invention herein is illustrated by means of a schematic diagram depicting a plant for the recovery of maleic anhydride from the gases produced in the production of phthalic anhydride.

Air is introduced through line 2 and is heated in the air preheater 1 and charged with o-xylene introduced through line 4 and already preheated in the heater 3. The o-xylene/air mixture is catalytically oxidized in the reactor 5 to produce phthalic anhydride. The reaction gas leaves the reactor 5 at a temperature of 380° C., passes through line 6 to reach the gas cooler 7, in which it is cooled to 170° C. and then passes through line 8 to the separator 9. In the separator the gas stream is cooled to about 55° C., and the phthalic anhydride is separated in solid form. The reaction gas, essentially free of phthalic anhydride, leaves separator 9 through line 10. From time to time, the raw phthalic anhydride separated in the separator 9 is melted out, collected in vessel 11, and fed through line 12 to a purification unit (not shown).

The gas leaving the separator 9 through line 10 contains maleic anhydride, monocarbonic acids, and other volatile components. It is washed in a scrubber 30 with aqueous maleic acid solution, thus removing from the gas the aforementioned secondary products. The maleic acid solution is conducted in a cycle through the scrubbing apparatus. The residual gas leaving the scrubber 30 can be released into the atmosphere. The scrubbing solution, concentrated to 25% by weight maleic acid, passes through line 32 to the thin-layer evaporator 33, in which the solution is concentrated under a vacuum to 100% by weight maleic acid. The approximately 100% maleic acid reaches the dehydrator 35 having a column put on. In this dehydrator, the maleic acid is decomposed under a vacuum into maleic anhydride and water vapor, which leave the dehydrator over the head, leaving residue as a bottoms product. The residue is intermittently withdrawn from the dehydrator. The maleic anhydride from the dehydrator is condensed in the condenser 36 and passes via line 38 to the pure maleic anhydride distillation column 39. In column 39, the maleic anhydride is distilled under a vacuum. The overhead vapors from column 39 are condensed in condenser 40; the pure maleic anhydride is drawn off at 42. From time to time, the residues are removed from the bottom of distillation column 39. The water vapor resulting from the evaporation of the maleic acid solution in the thin-layer evaporator 33 and from the dehydration of maleic acid in the dehydrator 35 is condensed in surface condenser 43 or 44 connected to vacuum lines 34 and 37. The resulting water is fed through lines 47, 48 and collecting line 49 to the waste gas scrubbing tower 30. The residual gas leaving the condensers 43, 44 is fed through lines 45 and 46 to the jet pumps 20 and 21, which maintain the desired vacuum. Preferably the gas fed to jet pump 20 through line 45 contains no more than about 35–40% by volume of water vapor and no more than 60–65% by volume maleic anhydride. Preferably the gas fed to jet pump 21 through line 46 contains no more than about 85–90% by volume water vapor and no more than about 10%–15% by volume maleic anhydride.

The pure distillation column 39, with condenser 40, is directly attached, by way of vacuum line 41, to the air jet pump 22, which maintains the desired vacuum. To simplify the diagram, each stage has been provided with only one air jet pump; in practice two air jet pumps can in each case be connected in series. The air jet pumps are operated with pressurized air at 6 atmospheres, which is conducted to the air jet pumps through line 26, through a heat exchanger 27 where the air is heated with condensing steam, and through the branch lines 26$^a$, 26$^b$, and 26$^c$. The air from the air jet pumps, which is admixed and loaded with vapors sucked from apparatus 33, 35, and 39, is collected in line 28, which is connected to the gas line 10 leading from the separator 9 to the scrubber 30, so that the air loaded with vapors, along with the waste gases from the separator 9, are fed together into the scrubber 30.

EXAMPLE I

In a plant for the production of phthalic anhydride from o-xylene, 120,000 Nm$^3$/hr. (Nm$^3$/hr. is m$^3$/hr. at standard temperature and pressure) waste gas are obtained downstream of the phthalic anhydride separators of the plant as described in the drawing. This quantity of waste gas still contains maleic anhydride and other volatile organic compounds. The waste gas is scrubbed with a 25% by weight maleic acid solution at about 40° C. Of this scrubbing solution conducted in a cycle, 2.56 metric tons/hr. containing about 25% by weight maleic acid, is drawn off and evaporated in a thin-layer evaporator at 135° C. under a pressure of 450 mm Hg., up to about 100% by weight maleic acid. About 0.61 metric tons/hr. of this maleic acid is obtained, which is then further dehydrated in a stirring vessel having a column put on at 130° C. under 80 mm Hg. The resulting maleic anhydride vapors are condensed at temperatures of 80° C. About 0.40 metric tons/hr. of predistilled maleic anhydride is obtained, which is then subjected to pure distillation at 135° C. under a pressure of 80 mm Hg. The result is 0.38 metric tons/hour pure maleic anhydride.

To produce the vacuum needed for the thin-layer evaporator, the dehydrator, and the maleic anhydride pure distillation unit, air jet pumps are used which are operated at 6 atmospheres with air preheated to 150° C. About 30 Nm$^3$/hr., 120 Nm$^3$/hr., and 70 Nm$^3$/hr. air are used in the three stages, thereby providing a total of 220 Nm$^3$/hr. The vapor-charged air sucked from the evaporation, the dehydration and the pure distillation unit, together with the waste gases from the phthalic anhydride separators, are introduced into the scrubbing zone. In the surface condensers about 1.8 metric tons/hr. water are produced, which is employed in scrubbing the waste gases leaving the phthalic anhydride separators. The costs for the air jet suction unit in the three stages and the surface condensers represent about 2.5% of the total apparatus costs.

EXAMPLE II (Comparative Example)

A process similar to that described in Example I is carried out except that steam jet pumps are used instead of air jet pumps. Saturated steam at 6 atmospheres is used as a propellant. The steam is condensed in injection condensers. The cooling water necessary to condense the steam is conducted in a cycle, and the condensation heat is indirectly removed in a heat exchanger. To operate the steam jet pumps of the three stages, about 0.3 metric tons/hr. steam are necessary, as well as 19 m$^3$/hr. cooling water for the condensation of the steam. About 5 metric tons/hr. excess weak acid is produced at the steam jet pumps which contains about 2% by weight maleic acid, and is employed in scrubbing the waste gases leaving the separator. From the scrubbing acid cycle, 2.56 metric tons/hr. of scrubbing solution, containing about 25% by weight maleic acid, is drawn off. The larger quantity of water, 5 metric tons/hr. as compared to 1.8 metric tons/hr. in Example I when air jet suction units are employed, is introduced into the scrubbing cycle and is balanced out by a reduced input of fresh water into the scrubbing cycle. The costs of the steam jet units of the three stages with the appurtenant condensers, cooler, and regulating equipment, represent about 8% of the total apparatus costs.

In addition to the advantages of using air jet suction units as illustrated by these examples, there are other positive features of the present invention. For example, the consumption of electrical energy is reduced by about 30% by virtue of the elimination of the weak-acid cycle. Furthermore, the entire plant consumption of cooling water is reduced by the amount needed for the condensation of propellant steam, which is about 10%. A further advantage results from the fact that the condensates produced in the surface condensers can be introduced into the scrubbing system of the phthalic anhydride unit at a higher temperature than the weak acid produced in the weak-acid cycle. Thus, the temperature of the water in the scrubbing system of the phthalic anhydride unit can be easily increased, which in turn favorably affects the solubility of phthalic anhydride in the maleic acid solution.

What is claimed is:

1. In a process for recovering maleic anhydride from a maleic anhydride-containing reaction gas, whereby (a) said maleic anhydride-containing reaction gas is contacted in a scrubbing zone with a scrubbing solution which is water or an aqueous maleic acid solution, (b) said scrubbing solution containing maleic acid is thereafter concentrated in a concentration zone and dehydrated in a dehydration zone to thereby form maleic anhydride which is then purified by distillation in a distillation zone, and (c) said concentration, dehydration and distillation steps being performed under a vacuum maintained by withdrawing vapor-containing gases from said concentration, dehydration and distillation zones using the suction of jet pumps, the improvement which comprises:

(A) employing pressurized air as a propellant for said jet pumps;

(B) admixing said propellant air with said vapor-containing gases removed from said concentration, dehydration and distillation zones; and (C) introducing said admixture of propellant air and suction-removed, vapor-containing gases into said scrubbing zone.

2. A process in accordance with claim 1 wherein said pressurized air is preheated to a temperature of from about 30° C. to 200° C. before said air is admixed with said vapor-containing gas.

3. A process in accordance with claim 2 wherein said pressurized air is preheated to a temperature of from about 100° C. to 200° C.

4. A process in accordance with claims 1, 2 or 3 wherein said pressurized air propellant is employed in said jet pumps at a pressure of from about 2 to 20 atmospheres.

5. A process in accordance with claim 4 wherein said pressurized air propellant is employed at a pressure of from about 4 to 10 atmospheres.

6. A process in accordance with claim 1 wherein maleic anhydride recovered is stored in maleic anhydride storage vessels; wherein vapor-containing gases from said storage vessels are removed by suction from the jet pumps, and wherein said vapor-containing gases are introduced into the scrubbing zone for the maleic anhydride-containing reaction gas.

7. A process in accordance with claim 1, 2 or 6 wherein (A) water and maleic anhydride are condensed from the vapor containing gases withdrawn from the concentration zone to the extent that such gases contain no more than about 40% by volume of water vapor and no more than about 65% by volume maleic anhydride before said concentration zone gases are admixed with propellent air; and (B) water and maleic anhydride are condensed from the vapor-containing gases withdrawn from the dehydration zone to the extent that such gases contain no more than about 90% by volume of water vapor and no more than about 15% by volume of maleic anhydride before said dehydration zone gases are admixed with propellant air.

* * * * *